United States Patent [19]

Honkawa et al.

[11] 4,055,395
[45] Oct. 25, 1977

[54] ANALYSIS APPARATUS

[75] Inventors: Tadashi Honkawa; Kenji Fukuda; Mikio Shimizu, all of Ibaraki, Japan

[73] Assignee: Hitachi, Ltd., Tokyo, Japan

[21] Appl. No.: 737,094

[22] Filed: Oct. 29, 1976

[30] Foreign Application Priority Data

Oct. 31, 1975 Japan .................................. 50-130404

[51] Int. Cl.$^2$ ........................................... G01N 21/24
[52] U.S. Cl. ................................. 23/253 R; 250/343; 356/244
[58] Field of Search ............. 23/253 R, 259; 356/244, 356/178; 250/343

[56] References Cited

U.S. PATENT DOCUMENTS

| | | | |
|---|---|---|---|
| 3,665,980 | 5/1972 | Croslin et al. ........................ | 23/259 |
| 3,703,336 | 11/1972 | Rosse et al. ...................... | 23/253 R X |
| 3,770,354 | 11/1973 | Tsuruta et al. ....................... | 356/178 |
| 3,877,817 | 4/1975 | Ralston .......................... | 23/253 R X |

Primary Examiner—Robert M. Reese
Attorney, Agent, or Firm—Beall & Jeffery

[57] ABSTRACT

In a biochemical analysis apparatus, two kind of cuvettes are used, one having a single chamber and the other having three chambers joined. These cuvettes are incubated at a predetermined temperature in incubator chambers of the analysis apparatus one after another, and the period of the incubation is determined depending on the above kind of the cuvettes. After the completion of incubation the cuvette is set in a measuring chamber of a photometry section of the analysis apparatus. In the photometry section, two paris of photosensors are provided for detecting the light of various wave length which passes through the measuring chamber, and either one of the two pairs of photosensors is automatically selected according to the kind of the cuvette set in the measuring chamber. Ouput signals from a pair of the photosensors are calculated automatically and the result of the calculation is indicated on an indicator of this apparatus.

9 Claims, 8 Drawing Figures 4,055,395

ANALYSIS APPARATUS

BACKGROUND OF THE INVENTION

This invention relates to an analysis apparatus, more particularly to a biochemical analysis apparatus.

A need increases for instruments that produce accurate chemical analysis data. In particular, biochemical analysis data, such as those of glucose, urea, glucose oxaloacetete transaminase (GOT) etc. that are contained in blood or other body fluid, would assist doctors in diagnosing the illness of patients. For this purpose a photometric analysis is frequently employed. In accordance with a conventional photometric analysis the analytical determination is made directly by comparison of sample with a standard or by observing the rate of chemical change of sample processed. Such technique is frequently employed in the analysis of the blood or the other body fluid. In the above mentioned photometric analysis, however, various conditions and modes are required corresponding to the tests. For example, the determination of the glucose requires a sample that is completely incubated at a temperature of 100° C for 20 minutes and the measurement by the light of 6400 Angstrom, while that of the GOT requires a sample that is completely incubated at a temperature of 37° C for 15 minutes and the measurement by the light of 5250 Angstrom. The analysis instrument, therefore, which can be easily operated by unskilled persons has been developed. One of such improved instruments is disclosed in U.S. Pat. No. 3,703,336. In this instrument, a card with the information of the test to be performed and a card reader are utilized for automatic incubation and measurement. That is, the period and the temperature of the incubation and the photo-filter wheel selecting the light of specific wave length are controlled according to the information on the card. Such analysis instrument, however, has drawbacks that it is expensive and complex in the structure because of the card reader provided therein.

SUMMARY OF THE INVENTION

An object of the invention is to provide an analysis apparatus by means of which unskilled persons can easily perform the test.

Another object of the invention is to provide an analysis apparatus of low cost.

This analysis apparatus is capable of executing two modes of chemical analyses, and specific reagents are used for each of the tests performed therewith. The tests are divided into two groups, each group of which requires a corresponding period of incubation at a predetermined temperature. The analysis apparatus for performing the chemical analysis which is above mentioned comprises containers, each of which has at least one chamber containing specific reagent and a form thereof depending on the analysis to be performed, incubator chambers for heating said containers for various periods each at a predetermined temperature depending on the forms of said containers one after another, measuring chamber in which said container completely incubated is inserted, and photometry means comprising (a) a light source for radiating light of various wave length, (b) photometric measuring means for detecting the light which passes through said measuring chamber, (c) a circuitry means having a first circuit for detecting the form of said container inserted into said measuring chamber and for selecting the light to be detected by said photometric measuring means depending on the form of said container, and a second circuit for calculating signals from said photometric measuring means, and (d) an indicator on which the calculated result of said second circuit of said circuitry means appears.

BRIEF DESCRIPTION OF DRAWINGS

FIG. 1 (b) is a sectional view of the biochemical analysis apparatus taken along the line A—A of FIG. 1 (a);

FIG. 1 (c) is a sectional view of the biochemical analysis apporatus taken along the line B—B of FIG. 1 (a);

DETAILED DESCRIPTION OF THE PREFERRED EMBODIMENT

Figure 1A:
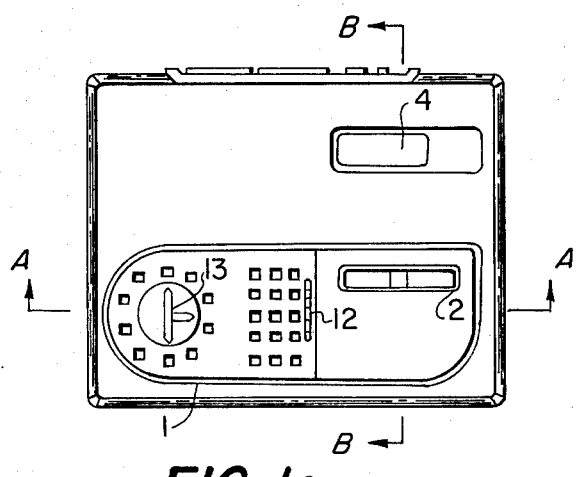
FIG. 1 (a) is a top plan view of a biochemical analysis apparatus constructed in accordance with the invention.
Figure 1B:
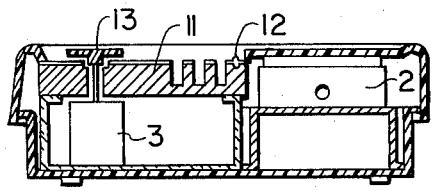
Figure 1C:
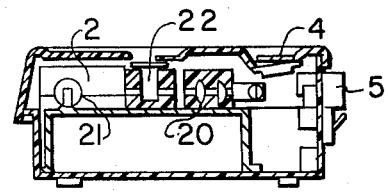

Referring now to FIGS. 1 (a),(b) and (c), there is shown an analysis apparatus including an incubation section 1 in which samples to be tested are incubated. The incubation section 1 has a heat block 11 on which two groups of incubator chambers are disposed, a thermometer 12 and a timer 13. One of the two groups of the incubator chambers is disposed around the timer 13 and the other group thereof is disposed to the right of the heatblock 11. The heatblock 11 is made of light metal, such as alminum, and is maintained at a certain temperature. In this embodiment, the heatblock 11 is heated at 37° C by a panel heater which is laid on surrounding thereof. The current flowing through the panel heater is controlled by a thermal element so that the temperature of all incubator chambers of the incubation section 1 are maintained at 37° C. The thermometer 12 is mounted on the right of the heatblock 11 and indicates the temperature thereof. The timer 13 includes a motor 3 which rotates a shaft thereof at a constant speed. In this embodiment, the timer 13 takes 10 minutes to make a round.

A photometry section 2 includes a tungsten lamp 21 as a light source and a measuring chamber 22. After the completion of the incubation by the incubation section 1, the sample to be tested is inserted into the measuring chamber 22. The photometric measurement of the sample is performed automatically by a photometer section 20. In this embodiment, the photometer section 23 has changable photometric modes which are automatically selected according to the form of a cuvette. The results of the photometric measurement are sent from the photometer section 20 to an electric circuitry section 5 as electric signals. The electric circuitry section 5 processes the results from the photometer section 20 in the prodetermined manner and indicates the calculated result on a digital indicator 4. The electric circuitry also controls the photometer section 20.

Figure 2A:
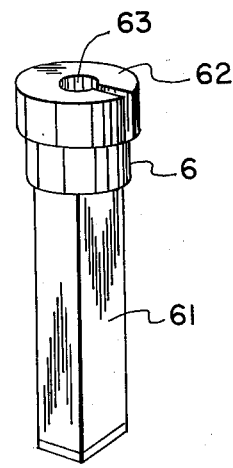
FIG. 2 (a) and (b) show pictorical views of a single cuvette and a three joined cuvettes respectively.
Figure 2B:
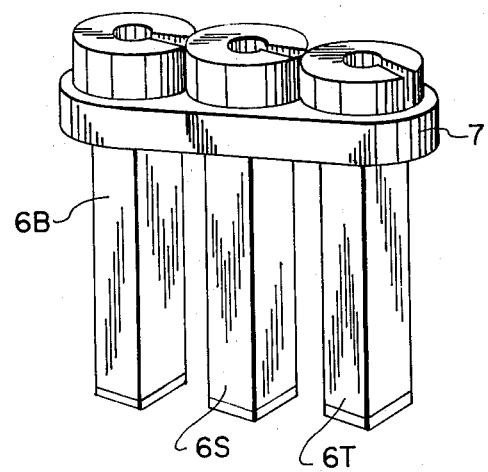

Referring to FIG. 2 (a), there is shown a single cuvette 6 used in the analysis apparatus. For the test which is performed by a rate assay mode, the single cuvette 6 is used. The sample and reagent are contained in a chamber 61 which is made of transparent material, for example glass or plastic through which light of wave length longer than 300 nm can pass. The dimension of the chamber of each cuvette must be sized accurately and the thickness of the wall material should be uniform among different cuvettes so that the absorption of light can be kept at an equal rate with respect to the same sample in different cuvettes. The cuvette 6 may previously contain liquid reagent or freeze-dried reagent in the chamber 61 thereof. In the later case, the freezed-dry reagent must be resolved by adding a desired amount of distilled water. The sample to be tested, for example serum of a patient, is added through a duct 63 of a cap 62 which is mounted on the cuvette 6.

Referring to FIG. 2 (b), there is shown three cuvettes which are joined to one another by a binder 7. The three joined cuvettes, each of which is the same as the single cuvette 6 described above, is used for tests which are performed by an end point assay mode. The three joined cuvette includes three cuvettes 6B, 6S and 6T. The cuvette 6B which contains nothing is used as a "blank"; the cuvette 6S which contains standard liquid is used as a "standard"; the cuvette 6T which contains the sample to be tested is used as a "sample" holder.

Figure 3:
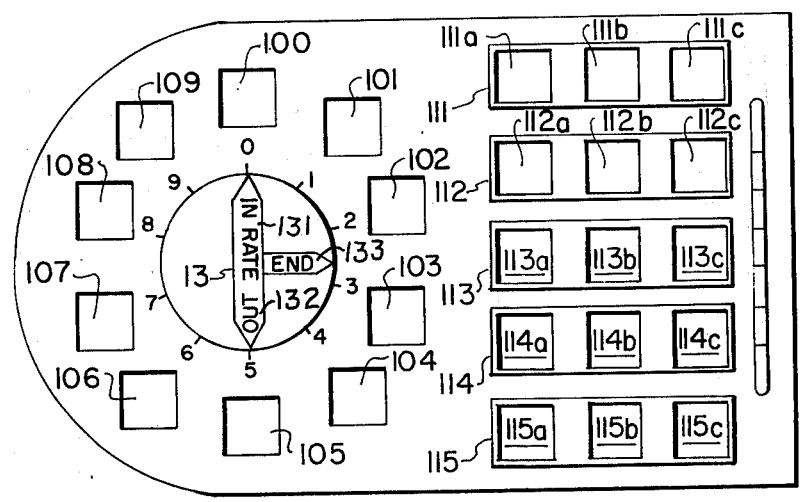
FIG. 3 is a top plan view of an incubation section of the biochemical analyses apparatus.

Referring to FIG. 3, there is shown the arrangement of the incubator chambers which are disposed on the heatblock 11 of the incubator section 1. As described above, ten incubator chambers 100 to 109 are disposed around the timer 13 at equal spacings from one another, which are annexed by one of a series of numbers "0" to "9" clockwise in series. These incubator chambers 100 to 109 are used for the incubation of the sample contained in the single cuvette 6 which is tested by the rate assay mode.

The other group of the incubator chambers disposed in the right side of the heatblock 11 includes five lines of the incubator chambers 111 to 115; and each line thereof includes three incubator chambers, for example, 111a to 111c. The incubator chambers of the five lines 111 to 115 are used for the incubation of the sample contained in the three joined cuvettes which is tested by the end point assay mode.

The timer 13 has three indicators including an "IN" indicator 131, an "OUT" indicator 132 and an "END" indicator 133. The "IN" indicator 131 and the "OUT" indicator 132 are used for the test of the rate assay mode and the "END" indicator 133 is used for the test of the end point assay mode.

Figure 4:
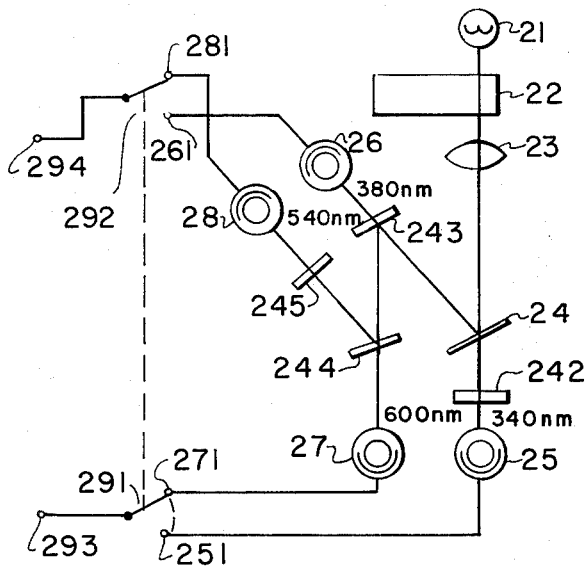
FIG. 4 is a schematic diagram of a photometry section of the biochemical analysis apparatus.

Referring now to FIG. 4, there is shown the arrangement of the photometry section 2 includes the measuring chamber 22 in which the single cuvette or the three joined cuvettes are inserted to perform the photometric measurement. The white light from the tungsten lamp 21 passes through the measuring chamber 22 and thereafter is condensed by a lense 23 of the photometer section 20. The condensed light beam reaches a surface of a halfmirror 24 at an angle of 30° to a perpendicular line thereof. The light of a certain wave length contained in the light beam passes through the halfmirror 24 and reaches a surface of a first photosensor 25 through a first photofilter 242. The photofilter 242 is previous mainly to the light of 340 nm. The halfmirror 24 is made of glass, on the surface of which aluminum is vacuum-evaporated semi-opaquely or cross slits are provided. The light beam reflected by the halfmirror 24 reaches a second photofilter 243 at an angle of 30° to a perpendicular line thereof. Light of 380 nm passes through the photofilter 243 and reaches a second photosensor 26. The light beam of remaining wave length which is reflected by the second photofilter 243 reaches a third photofilter 244 at an angle of 30° to a perpendicular line thereof. The light of 600 nm. passes through the third photofilter 244 and reaches a third photosensor 27. The light beam reflected by the third photofilter 244 reaches a fourth photofilter 245 at a right angle. The light of 540nm passing through the photofilter 245 reaches a fourth photosensor 28. These photosensors 25 to 28 include photoconductive semi-conductors in this embodiment, or may be photomultipliers.

Each of the photosensors 25 to 28 produces an output signal at terminals 251, 261, 271 and 281 respectively. A pair of the terminals 251 and 271 are connected to input terminal 293 of the circuitry section 5 of the apparatus through a first contact switch 291 and the other pair of the terminals 261 and 281 are connected to another input terminal 294 thereof through a second contact switch 292. The first and second contact switches 291 and 292 cooperate with each other. That is, the contact switches 291 and 292 are brought into contact with the terminals 251 and 261 respectively when the test is performed by the rate assay mode. While the contact switches 291 and 292 are brought into contact with the terminals 271 and 281 respectivly when the test is performed by the end point assay mode.

A variety of biochemical analysis may be performed with this apparatus. The following tables indicate typical examples of the tests that may be performed with this apparatus.

Group I

| test | method | reagent |
| --- | --- | --- |
| alkaline-phosphatase | L-naphthol | Al-P . HI-STAT |
| urea nitrogen | urease | BUN . HI-STAT |
| creatinine-phosphokinase | Rosalki | COK . HI-STAT |
| glutamate oxalo-acetate transaminase | Henrry | GOT . HI-STAT |
| glutamate pyruvate transaminase | Henrry | GPT . HI-STAT |
| L-hydroxyburate dehydrogenase | Rosalki | HBD . HI-STAT |
| lactate dehydrogenase | Waccur | LDH . HI-STAT |

For each of these tests performed by the rate assay mode, the serum of 50 µl and the incubation of five minutes at the temperature of 37° C are necessary.

Group II

| test | serium (µl) | method | reagent |
| --- | --- | --- | --- |
| albumin | 50 | B.C.P. | ALB . HI-STAT |
| bilirubin | 50 | diazo | BIL . HI-STAT |
| calcium | 50 | MTB | CA . HI-STAT |
| cholesterol | 50 | enzyme | CHO . HI-STAT |
| glucose | 50 | enzyme | GLU . HI-STAT |
| total protein | 50 | bieuret | TP . HI-STAT |
| hemoglobin | 20 | cyanemetho-hemoglobin | HB . HI-STAT |

For each of these tests performed by the end point assay mode, the serum of 50 µl, except the hemoglobin test which requires the serum 20 µl, and the incubation of ten minutes at the temperature of 37° C.

These reagents mentioned above are produced by International Reagents Corporation in Japan and are on sale as HI-STAT reagents.

Illustrative examples of the test modes are given hereinafter with reference to FIG. 3. For each test of the group I, the rate assay mode is performed. In the rate assay mode, the single cuvette is used for each sample to be tested. The tests of group I including the alkaline-phosphatase test and the urea nitrogen test are as follows. After adding 50 μl of the serum of the patient into the chamber of the single cuvette which contains 1.5ml of the specified liquid reagent, for example the liquid AL-P-HI-STAT reagent, the single cuvette is inserted into the incubator chamber 100 when the "IN" indicator 131 faces the number "0" which is one of the numbers around the timer 13. The timer 13 rotates at the constant rotating speed as mentioned above. One minute later when the "IN" indicator 131 comes to face the number "1", the next single cuvette is inserted in the next incubator chamber 101. The liquid BUN-HI-STAT reagent must be completely mixed with the serum by that time. Succeeding cuvettes to be tested by the rate assay mode are inserted into the remaining incubator chambers 102 to 109 every 1 minute in the same way as above mentioned.

The "OUT" indicator 132 indicates the completion of the incubation. Five minutes after the first cuvette was inserted in the incubator chamber 100 when the "OUT" indicator 132 comes to face the number "0", the cuvette of the alkaline-phosphatase test which is completely incubated is pulled out of the incubator chamber 100 and is set into the measuring chamber 22 of the apparatus. The photometry section 2 automatically performs the photometric measurement of the cuvette to be tested and the result of the photometric measurement which is calculated in the circuitry section 5 is indicated on the indicator 4. Therefore, the tests performed by the rate assay mode are efficiently and easily achieved every one minute with the apparatus.

For each test of the group II, the end point assay mode is required. In the end point assay mode, a set of the three joined cuvettes is used. The "standard" cuvette 6S and the "sample" cuvette 6T of the three joined cuvettes shown in FIG. 2 (b) contain the specified liquid reagent, for example ALB-HI-STAT specified for the albumin test. After adding 50 μl of the serum of a patient into the chamber of the "sample" cuvette, the set of the three joined cuvettes is inserted into one of the lines of the incubator chambers 111 to 115 when the "END" indicator 133 of the timer 13 faces the number "0". Two minutes later, when the "END" indicator 133 comes to face the number "2", the next set of the three joined cuvettes is inserted into the next line of the inculator chambers 112. Succeeding sets of the three joined cuvettes to be tested by the end point assay mode are inserted into the remaining lines 113 to 115 every 2 minutes in the same manner as above mentioned.

Ten minutes after the first set of the three joined cuvettes was inserted into the line of the incubator chamber 111, the "END" indicator 133 comes to face the number "0" and the first set of the three joined cuvettes for the albumin test which is completely incubated by that time is pulled out of the line of the incubator chambers 111 and is inserted into the measuring chamber 22 of the apparatus. The photometry section 2 automatically performs the photometric measurement of the three joined cuvettes and the result of the measurement calculated in the circuitry section 5 is indicated on the indicator 4 of the apparatus. Therefore, the tests of the group II are efficiently and easily achieved every two minutes with the apparatus.

Figure 5:
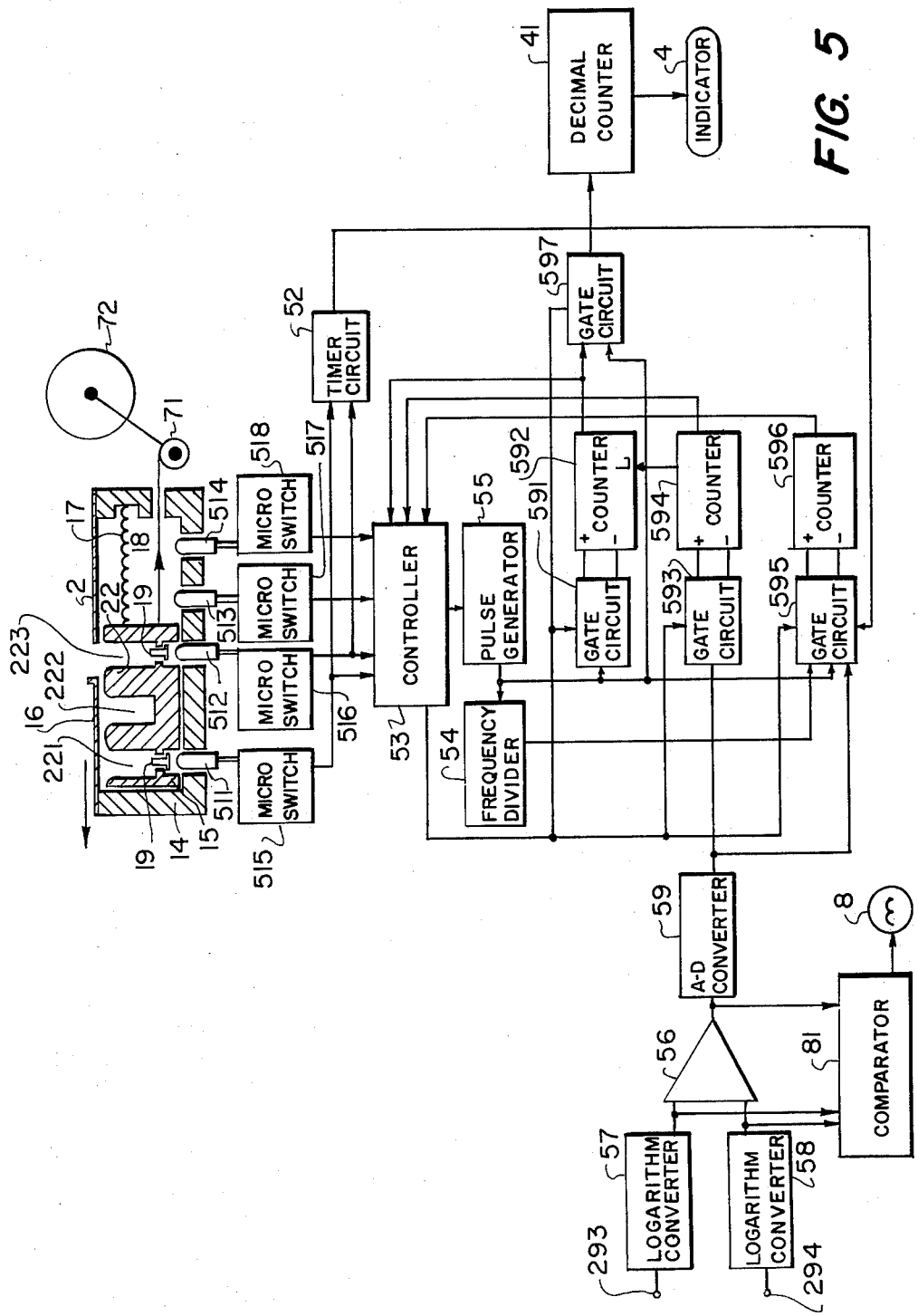
FIG. 5 is a schematic diagram of a circuitry section of the biochemical analysis apparatus.

Referring now to FIG. 5, there are illustrated the schematic diagram of the circuitry section 5 and the sectional view of the photometry section 2 including a casing 14 and a slidable cuvette holder 15 having measuring chambers 15. The cuvette holder 22 has three measuring chambers 22, namely 221, 222 and 223, two of which are covered by a measuring chamber covering 16 which may be slipped toward the left when the three joined cuvettes assembly is inserted therein. The cuvette holder 15 is biased to the left by a spring 17 and is pulled toward the right by a string 18 which is secured on a pully 71 mechanically connected to and driven by a shaft of a motor 72. At the bottoms of the chambers 221 and 223, there are provided pins 19 respectively. Each of the pins 19 is depressed downward upon the insertion of the cuvette. Levers 511, 512, 513 and 514 are provided on the bottom of the casing 14 each of which is mechanically connected to corresponding microsmitches 515, 516, 517 and 518. That is, each of the microsmitches 515, 516, 617 and 518 is closed when the corresponding levers 511, 512, 513 and 514 are depressed downward. The white light from the lamp 21 which is shown in FIG. 4 passes through the chamber 223 in the position on the holder 15 as shown in FIG. 5.

The input terminals 293 and 294 which are connected to the photometry section shown in FIG. 4 are connected to logarithm converters 57 and 58 at input terminals thereof respectively. Each output terminal of the logarithm converters 57 and 58 is connected to a differencial amplifier 56 and a comparator 81. An output terminal of the differential amplifier 56 is connected to the comparator 81 which has an output terminal connected to an indicator lamp 8. The comparator 81 compares the output signal of the differential amplifier 56 to each of the output signals from the logarithm converters 57 and 58 and generates an output signal to the indicator lamp 8 when the difference between the signals thereof exceeds a predetermined value. The output terminal of the differential amplifier 56 is further connected to an analogue-digital (A-D) converter 59 which generates frequency signal according to the output voltage from the differential amplifier 56.

A controller 53 to which the output terminals of the microswitches 515, 516, 517 and 518 are connected controls four gate circuits 591, 593, 595 and 597. The output terminals of the microswitches 515 and 516 are further connected to a timer circuit 52. The timer circuit 52 generates control signal to the gate circuit 595 every fifteen seconds when only the microswitch 516 is pushed down, i.e. the single cuvette is inserted into the measuring chamber, and it is inhibited when both of the microswitches 515 and 516 are pushed down by the three joined cuvettes The contoller 53 further initiates a pulse generator 55, an output terminal of which is connected to input terminals of the gate circuits 591, 595 and 597 and a frequency divider 54. The frequency divider 54 divides the pulse train from the pulse generator 55 into a pulse train of less ferquency than that, i.e. the frequency of the pulse train from the pulse generator 55 is decreased to one-hundredth through the frequency divider 54 in this embodiment. The output terminal of the frequency divider 54 is connected to the gate circuit 595. The output terminal of the A-D converter 59 is connected to the gate circuits 593 and 595. Each of the gate circuits 591 and 593 connects one of the output terminals thereof to a plus input terminal or a minus input terminal of corresponding counters 592 and 594 according to the control signal from the controller 53. The gate circuit 595 connects one of the output terminals thereof to a plus input terminal or a minus input terminal of the counter 596 according to the control signals from the controller 53 and timer circuit 52. Output terminals of the counters 592, 594 and 596 are connected to the controller 53. The output terminal of the counter 592 is further connected to the gate circuit 597 at another input terminal. The other output terminal of the counter 594 is connected to the counter 592 so that counted number stored in the counter 594 is transmitted to the counter 592. Output terminal of the gate circuit 597 is connected to a decimal counter 41 which counts the number of pulses and indicates the counted number on the indicator 4.

The operation of the above mentioned circuitry is given hereinafter. When the single cuvette is inserted into the chamber 223 of the cuvette holder 22, the microswitch 516 is closed and the controller 53 brings the switches 291 and 292 shown in FIG. 4 into contact with the terminals 251 and 261 respectively. The output signals from the photosensors 25 and 26 (340nm, 380 nm) are led to the corresponding logarithm converters 57 and 58 through the terminals 293 and 294 respectively. Converted signals from the logarithm converters 57 and 58 are led to the two input terminals of the differential amplifier 56 which generates the output signal according to the difference between them. The differential signal is converted into the pulse signal through the A-D converter 59. At the same time, the timer circuit 52 generates a first control signal to the gate circuit 595 so that the pulse signal from the A-D converter 59 is led to the plus input terminal of the counter 596 until the next control signal is generated. The timer circuit 52 generates the second and the third control signals every fifteen seconds. The gate circuit 595 leads the pulse signal from the A-D converter 59 to the minus input terminal of the counter 596 upon the receipt of the second control signal and inhibits the pulse signal therefrom from being led to the counter 596 upon the receipt of the third control signal. That is, the pulse signal is led to the plus input terminal of the counter 596 during the first period of fifteen seconds and the pulse signal is led to the minus input terminal thereof during the second period of fifteen seconds. Therefore, the differential number between the pulse signals for the first period and that for the second period is stored in the counter 596. Then the controller 53 initiates the pulse generator 55 and generates a signal to the gate circuit 595 and 597 so that the pulse train from the pulse generator 55 is led to the minus input terminal of the counter 596 and the decimal counter 41. When the counted number of the counter 596 comes to zero, the counter 596 generates an output signal to the controller 53 which inhibits the pulse generator 55 from generating the pulse train. The decimal counter counts the pulses from the pulse generator and transfers the counted number to the indicator 4 for the indication.

When the three joined cuvettes are inserted in the cuvette holder 15 with the "sample" cuvette being in the chamber 221, the "standard" cuvette in the chamber 222 and the "blank" cuvette in the chamber 223, the microswitches 515 and 516 are closed and the controller 53 brings the switches 291 and 292 into contact with the terminal 271 and 281 respectively. At first, when the "blank" cuvette is in the path of the light from the lamp 21, the output signals from the photosensors 27 and 28 are processed into the pulse signal in the same way as mentioned above. The controller 53 generates a first control signal to the gate circuits 593 and 595 so that the pulse signal from the A-D converter 59 is led to the minus input terminals of the counters 594 and 596.

When the cuvette holder 15 is moved toward the right by the motor 72 and the "standard" cuvette is in the light path, the microswitch 517 is closed. The controller generates a second control signal to the gate circuits 593 and 595 so that the pulse signal from the A-D converter 59 is led to the plus input terminal of the counter 594 and inhibited from being led to the cunter 596. Assuming that the frequency of the pulse signal from the A-D converter 59 is Fb when the "blank" cuvette is in the light path and the frequency thereof is Fs when the "standard" cuvette is in the light path, the number represented as Fs—Fb is stored in the counter 594. At last, when the "sample" cuvette comes to be in the light path, the microswitch 518 is closed. The controller 53 generates a third control signal to the gate circuits 593 and 595 so that the pulse signal from the A-D converter 59 is led to the plus input terminal of the counter 596 and inhibited from being led to the counter 594. Assuming that the frequency of the pulse signal from the A-D converter 59 is Fx when the "sample" cuvette is in the light path, the number represented as Fx—Fb is stored in the counter 596. Then the controller initiates the pulse generator 55 and generates a fourth control signal to the gate circuit 591, 595 and 597. The pulse train from the pulse generator 55 is led to the plus input terminal of the counter 592, and the divided pulse train from the frequency divider 54 is led to the minus input terminal of the counter 596. The counter 592 sends its output signal to the decimal counter 41 through the gate circuit 597 and the number stored in the counter 594 is transmitted thereto, whenever the counted number of the counter 596 comes to zero. When the counted number of the counter of the counter 596 comes to zero, it generates an output signal to the controller 53 so that the pulse generator 55 stops generating the pulse signal. Therefore, the number represented as 100×(Fx—Fb/-Fs—Fb) is stored in the decimal counter 41 and the number is indicated on the indicator 4.

What we claim:

1. An analysis apparatus for performing various chemical analysis using containers, each of which has at least one chamber containing specific reagent and a form thereof depending upon the analysis mode to be performed, comprising:

means forming a plurality of incubator chambers for successively heating the containers for various periods of time at a predetermined temperature depending on the forms of the containers that correspond to the analysis mode;

means forming a measuring chamber for receiving the container after the incubation in the incubator chambers; and photometry means comprising a. a light source for radiating light of various wave length through said measuring chamber, b. photometric measuring means for detecting the light which passes through said measuring chamber and producing a correlated signal, c. circuitry means having a first circuit for detecing the form of the container inserted into said measuring chamber and for selecting the light to be detected by said photometric measuring means depending on the form of the container in the measuring chamber, and a second circuit for receiving signals from said photometric measuring means and transforming them into readable data, and d. indicator means receiving and displaying the readable data of said second circuit of said circuitry means.

2. An analysis apparatus as claimed in claim 1, wherein said photometric measuring means of said photometry means comprises at least four photosensor means selectively sensitive to respective specific wave lengths, said photosensor means being divided into at least two pairs for at least two analysis modes, respectively, and one of said pairs of said photosensor means becoming selectively operative to send its signals to said second circuit under the control of said first circuit depending upon the form of the container within said measuring chamber.

3. An analysis apparatus as claimed in claim 1, including two different forms of the containers respectively for two different analysis modes, one form having a single chamber and another form having three chambers.

4. An analysis apparatus as claimed in claim 3 wherein said measuring chamber is formed so as to selectively receive both said one form of container and said another form of container, with said single chamber of said one form and one of the three chambers of said another form being in identical positions with respect to said light source, and including means shifting said measuring chamber to succesively position the remaining two chambers of said another form in said position; said first circuit of said circuitry means having at least one sensor means for detecting the presence of a chamber, for both said one form and said another form, in said positon, and a second sensor means for detecting the presence of more than one chamber to distinguish between the one form and the another form.

5. An analysis apparatus as claimed in claim 1, wherein said means forming incubator chambers further comprises timer means for indicating successive completions of the incubations performed in separate incubator chambers, respectively.

6. An analysis apparatus as claimed in claim 5, wherein said means forming incubator chambers provides a plurality of incubator chambers equally spaced around said timer means.

7. An apparatus as claimed in claim 6, wherein said means forming incubator chambers provides a second plurality of said incubator chambers in a grouping separate from and spaced from said incubator chambers around said timer means, and having indicia respectfully associated therewith, and said timer means having a pointer and indicia means that are relatively moveable with respect to each other during the timing, which indicia means correspond respectively to the incubator chambers of said second grouping.

8. An analysis apparatus as claimed in claim 7, including two different forms of the containers respectively for two different analysis modes, one form having a single chamber and being of such an external shape as to be received within the incubator chambers around said timer means, and another form having three chambers with an external shape receivable only within the incubator chambers of said second grouping, so that said incubator chambers around said timer means are adaptable to incubation for a first analysis mode whereas said second grouping of incubator chambers is adaptable to incubation for a second analysis mode.

9. An analysis apparatus as claimed in claim 8 wherein said measuring chamber is formed so as to selectively receive both said one form of container and said another form of container, with said single chamber of said one form and one of the three chambers of said another form being in identical positions with respect to said light source, and including means shifting said measuring chamber to successively position the remaining two chambers of said another form in said position; said first circuit of said circuitry means having at least one sensor means for detecting the presence of a chamber, for both said one form and said another form, in said position, and a second sensor means for detecting the presence of more than one chamber to distinguish between the one form and the another form.

* * * * *